United States Patent [19]

Wisegerber

[11] Patent Number: 4,788,990

[45] Date of Patent: Dec. 6, 1988

[54] FLOSSER LOCKING MECHANISM

[76] Inventor: Lester R. Wisegerber, 38 Brown La., Dayton, Tex. 77535

[21] Appl. No.: 36,063

[22] Filed: Apr. 9, 1987

[51] Int. Cl.$^4$ ............................................. A61C 15/00
[52] U.S. Cl. ..................................... 132/324; 132/323
[58] Field of Search .............. 132/89, 91, 92 R, 92 A, 132/93

[56] References Cited

U.S. PATENT DOCUMENTS

| | | | |
|---|---|---|---|
| 1,274,423 | 8/1918 | Kristmann | 132/92 R |
| 1,417,518 | 5/1922 | Henerlau | 132/92 R |
| 1,468,942 | 9/1923 | Gamble | 132/92 R |
| 1,879,074 | 9/1932 | Cammack | 132/92 R |
| 1,990,404 | 2/1935 | Doner | 132/92 R |
| 3,871,393 | 3/1975 | Wharton | 132/92 A |

Primary Examiner—John J. Wilson
Attorney, Agent, or Firm—Arnold, White & Durkee

[57] ABSTRACT

A dental flosser which has a locking mechanism that effectively prevents slippage of floss string during use. Broadly speaking, the flosser includes a body and a handle threadably joined to the body. The locking mechanism includes a bore in the body through which the floss is threaded, a shoulder on the body, and a washer mounted on the body adjacent the bore. With the floss looped around the washer, threadably tightening the handle on the body compresses the floss between the shoulder and handle to prevent floss slippage. Preferably, the handle has a floss storage cavity and the body has an internal floss passageway extending to the tip of one of two prongs on the body. Loosening the handle allows floss to be drawn or dispensed from the one prong.

12 Claims, 2 Drawing Sheets

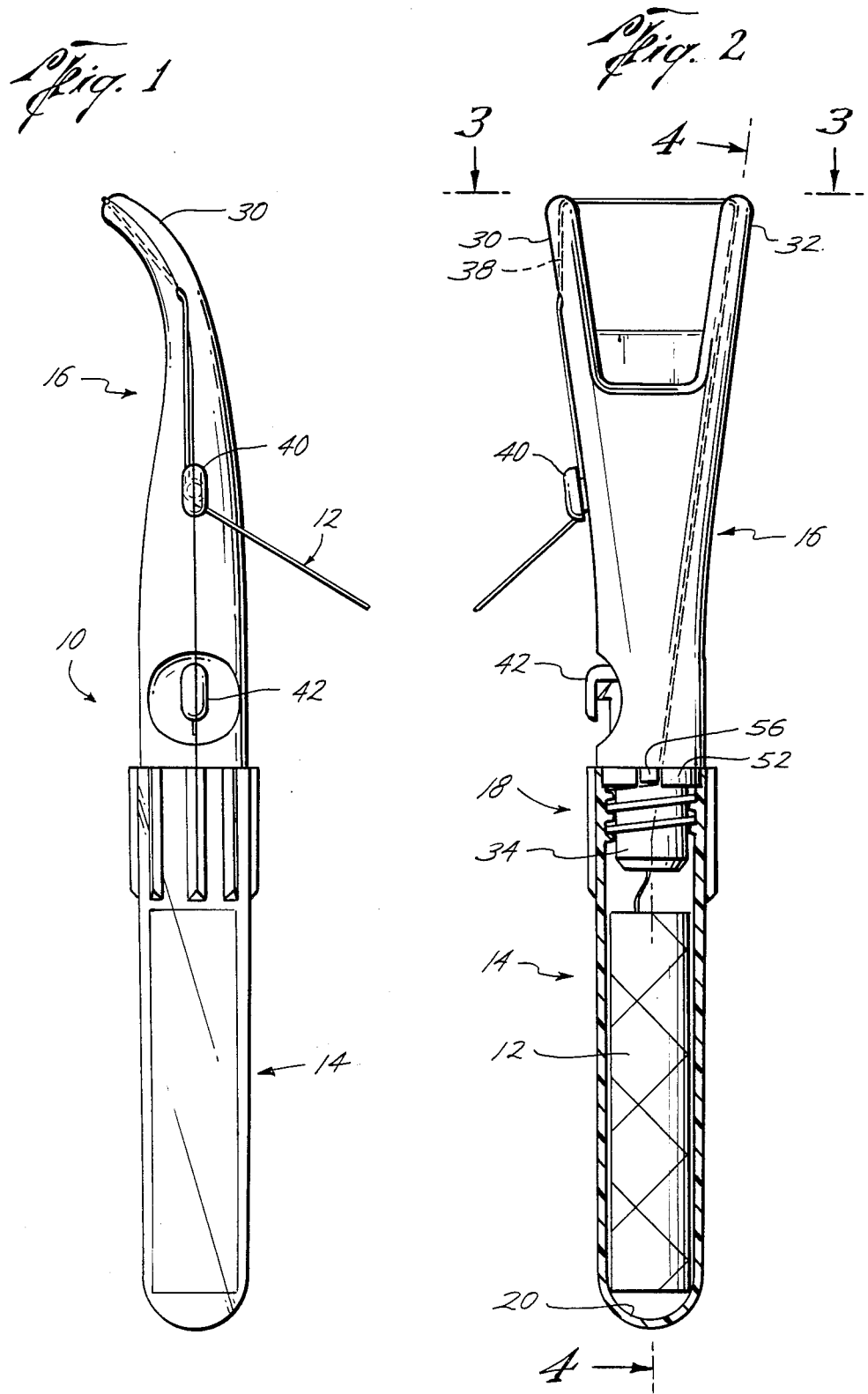

U.S. Patent Dec. 6, 1988 Sheet 2 of 2 4,788,990
Fig. 3
Fig. 4
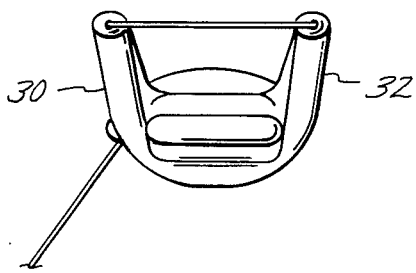
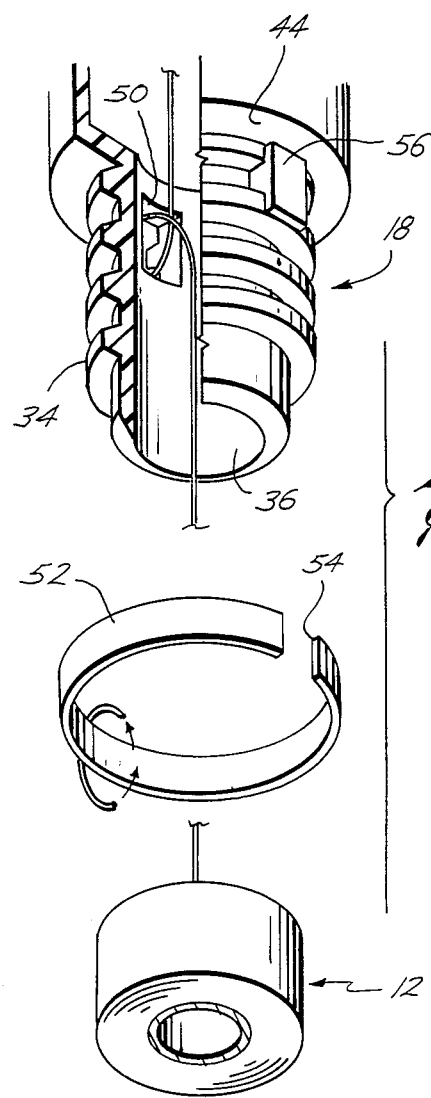
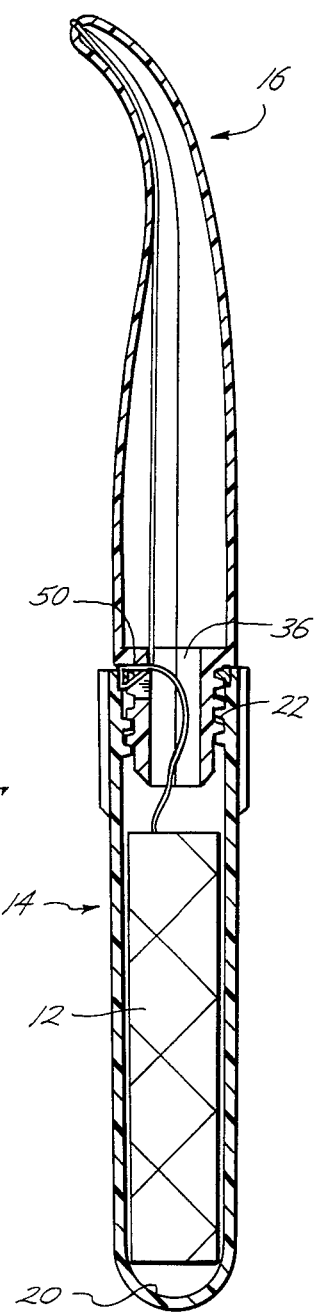
Fig. 5

FLOSSER LOCKING MECHANISM

BACKGROUND OF THE INVENTION

1. Field of the Invention

This invention relates to a hand held, dental flosser utensil. In particular, it relates to a locking mechanism on such a dental flosser which is selectable for dispensing new floss or locking the floss to prevent slippage.

2. Description of the Relevant Art

In recent years, dental flossing has assumed increasing importance as a method of preventing tooth decay. It has come to be appreciated that the removal of plaque between teeth is not accomplished by ordinary brushing and regular flossing contributes significantly to the removal of such plaque between teeth and under the gum. Plaque is a major cause of tooth decay and gum disease (pyorrhea) that, if allowed to build up, hardens and becomes tartar. Such periodontal disease is a serious cause of tooth loss. Normally, flossing is accomplished simply by grasping the floss string at two ends and working the floss between the teeth and gum using the appropriate hand motion.

There are, however, several difficulties with conventional flossing techniques. One difficulty is that the floss easily slips through the fingers during flossing operations unless the floss is wrapped securely around one or more fingers. Unfortunately, such wrapping can be discomforting to the fingers. A further difficulty is that typically a fairly large amount of floss is used to provide adequate regions to hold the floss string, while only a relatively small portion of the floss in the middle of the string is actually used in the flossing operation. That is, in conventional flossing techniques using the hands and fingers to hold the floss a large amount of floss is wasted. Finally, a particular problem with conventional hand flossing techniques is that such techniques not only requires moderate of hand dexterity, but additionally proper positioning of the floss is sometimes impossible because the hands cannot be properly positioned relative to the desired flossing location. Because of the need for moderate hand dexterity, the flossing operation is particularly difficult for certain people, such as those suffering from arthritis or the like.

Several floss devices have been proposed in the past which address some of the problems of conventional hand techniques for flossing. A common floss utensil has two prongs in which a string of floss is secured between each prong. Such a flossing apparatus is advantageous in that the floss utensil can be more easily placed in the mouth at the desired flossing location, does not waste as much floss, and can be used by those persons having minimal hand dexterity.

Still other types of floss utensils have been devised in which a supply of floss is actually stored within the floss utensil. One difficulty with such flossers that store the floss is preventing floss slippage during the flossing operation. To prevent slippage, such flossers typically include one or more upstanding studs around which the floss may be wrapped. That is, a portion of the floss is wrapped around the stud, the floss is then strung between the two spaced apart prongs, and the distal end of the floss is wrapped around the same or another stud. Examples of such flossers include the ez Denta-Flosser as made by pdp Company of Corona Del Mar, Calif.; the De-Plac dental flosser; and "The Flosser" as sold by *The Boston Proper* mail order catalog.

Still another type of hand held flossing utensil is the Floss-a-matic as sold by Dent-o-Care Products of Gardenia, Calif. In this floss utensil, the floss string is held in place during use by a slidable tension locking bar which transversely displaces the floss. U.S. Pat. No. 3,871,393 apparently relates to this type of flosser.

While such existing flosser utensils are an advance over the more conventional hand technique of flossing, they are nevertheless cumbersome in several respects. In particular, the floss dispensing procedure is somewhat complicated and even after performed does not always hold the floss to prevent shifting of the floss during the flossing operation. Thus, it would be an advance in the art if a floss utensil were devised in which the floss was self-contained, easily dispensed, and yet could be easily and effectively locked in place to prevent floss shifting during the flossing operation.

SUMMARY OF THE INVENTION

The problems outlined above associated with known floss utensils are generally solved by the dental flosser in accordance with the present invention. Broadly speaking, the flosser hereof includes a handle which has a cavity for holding the floss and an upper body having a pair of spaced apart prongs at one end and a shoulder at the other end. The handle and body are joined by a coupling mechanism such as complemental threads. A locking mechanism is provided for preventing the floss from slipping in the region of the joinder between the handle and the body. The locking mechanism includes a washer disposed between the shoulder and handle, the washer being adapted for receiving the floss looped around it. Thus, with the handle loose on the body, the floss can be dispensed, while with the handle tightened, the floss is secured in place between the handle, washer, and shoulder.

Preferably, the body has a floss-receiving passageway oriented longitudinally with the body and a floss-receiving bore oriented transversely to the body in communication with the passageway. Thus, the floss emerges from the cavity in the handle into the passageway, and exits through the bore where it is looped around the washer. Preferably, the passageway extends through one of the prongs so that with the handle loosened, the floss can be pulled from the prong and the floss slides easily around the washer and through the passageway. With the handle tightened, the floss is compressed between the joinder of the handle, washer, and shoulder, preventing longitudinal slipping movement of the floss. In a particularly preferred embodiment, the washer includes a notch and the body includes an upstanding boss adapted to engage the notch to prevent rotation of the washer when the handle is tightened.

BRIEF DESCRIPTION OF THE DRAWINGS

FIG. 1 is a side elevational view of the dental flosser in accordance with the present invention;

FIG. 2 is a front elevational view of the dental flosser hereof, with the handle portion in section and showing in phantom the path of travel of the floss string;

FIG. 3 is an end view of the dental flosser of the present invention taken along line 3—3 of FIG. 2;

FIG. 4 is a vertical sectional view with the flosser in the same general orientation of FIG. 1, taken along line 4—4 of FIG. 2; and FIG. 5 is an enlarged, exploded view in partial section of a portion of the locking mechanism of the present invention.

DESCRIPTION OF THE PREFERRED EMBODIMENTS

Turning now to the drawings, a dental flosser 10 for dispensing and holding the floss 12 is illustrated. Broadly speaking, the flosser 10 includes handle 14, body 16, and locking mechanism 18. In more detail, the handle 14 includes an internal cavity 20 for holding a spool of floss 12. End 22 of the handle 14 has an internal surface which is threaded and an external, outwardly facing surface which has upstanding elongated knurls.

The body 16 includes a pair of spaced apart prongs 30, 32 as shown in FIGS. 2 and 3. The end 34 of the body 16 (opposite the prongs 30, 32) is complementally threaded for joinder to the end 22 of the handle 14. An elongated floss-receiving passageway 36 extends from the threaded end 34 and through the prong 32. As shown in FIGS. 2 and 3, the prong 32 is apertured at one end while the prong 30 has a short channel 38 (FIG. 2) for stretching the floss 12 between the two distal ends of the prongs 30, 32. As shown in detail in FIGS. 1 and 2, the body 16 has an upstanding lock stud 40 around which the take-up distal end of the floss 12 is wrapped. Conveniently, a cutter 42 is provided proximate the lock stud 40 for eliminating excess floss. As can be seen in FIG. 5, an annular shoulder 44 rings the body 16 adjacent the threaded end 34.

Turning particularly to FIG. 5, the locking mechanism 18 is illustrated in some detail. As can be seen in FIG. 5, a bore 50 extends through the threaded end 34 into communication with the passageway 36 and generally transversely oriented thereto. An annular washer 52 slidably fits over the threaded end 34. The washer is notched as at 54 for engaging an upstanding boss 56 on the threaded end 34 (compare FIGS. 2 and 5).

In use, a spool of floss 12 is received in the cavity 20. As shown in FIGS. 2 and 4, the cavity 20 is in communication with the passageway 36 with the floss extending up the passageway 36 to a location adjacent the bore 50. The floss 12 is routed through the bore 50, looped around the washer 52, and inserted back into the passageway 36. As can be appreciated, several methods are available for looping the floss 12 about the washer 52, with the preferred method of loop being the wrap-around configuration illustrated with clarity in FIG. 5. The floss 12 extends through the passageway 36 (FIG. 2) emerging from the apertured distal end of the prong 32. The floss is stretched between the prongs 30, 32 and transcends the channel 38 where the distal end of the floss 12 is coupled about the lock stud 40.

To dispense floss, the handle 14 is threadingly loosened from the body 16 and the distal end of the floss 12 decoupled from the stud 40. The floss 12 is then pulled at the distal end (or adjacent prong 32) with the configuration of the locking mechanism 18 allowing the floss to be dispensed from the spool in the handle 14. When the desired amount of floss 12 is dispensed, the handle 14 is threadingly tightened, excess floss eliminated at cutter 42, and the distal end of the floss connected to the stud 40.

Tightening of the handle 14 shifts the washer 52 towards the shoulder 44. With the handle 14 tightened, the floss 12 is compressed between the handle 14, washer 52 and shoulder 44. Advantageously, the engagement of the notch 54 and boss 56 prevents rotation of the washer 52 during the tightening operation.

Those skilled in the art will appreciate that many alternatives exist to the preferred embodiment illustrated in the drawings without departing from the scope of the present invention. For example, the washer 52 primarily represents any longitudinally shiftable structure around which the floss 12 might be wrapped. The washer 52 could simply comprise a pin slidably received in a groove structure on the body 16. Further, it is not necessary that the handle 14 be integral with the threaded end 22, and a compression nut might be substituted for such structure. For that matter, although a threaded coupling of the handle 14 and body 16 is preferred, other types of coupling mechanisms are available and operable in accordance with a locking mechanism of the present invention.

I claim:

1. A dental flosser for dispensing and holding a string of floss comprising:

a handle including means for receiving floss;

an elongated body including a pair of spaced-apart prongs at one end, a shoulder at the other end, and an enclosed floss-receiving passageway extending within one of the prongs in operable communication with the floss receiving means;

means for coupling the other end of the body to the handle adapted for longitudinally extending the floss from the handle to the floss-receiving passageway; and locking means for preventing the floss from slipping in the region of the coupling means, including a washer disposed between said shoulder and handle and adapted for receiving floss looped therearound, the locking means being configured such that the floss can pass from the handle, loop around the washer, and pass into the floss-receiving passageway without being exposed outside the flosser, the coupling means being operable for compressing the washer such that with the floss looped around the washer, the floss is compressed between the washer and the handle and between the washer and the shoulder, preventing slipping movement of the floss in the region of the washer.

2. A dental flosser in accordance with claim 1, wherein said floss receiving means comprises structure defining a cavity within the handle.

3. A dental flosser in accordance wih claim 2, wherein the coupling means includes complementally threaded portions adjacent the other end of the body and one end of the handle.

4. The flosser in accordance to claim 1, including structure defining a bore extending generally transversely through the body other end and in communication with said passageway for receiving the floss therethrough.

5. The flosser in accordance with claim 4, said washer being annular and having opposed, radial inward and radial outward surfaces and opposed side surfaces, said washer being disposed between the shoulder and handle relative to said bore for receiving the floss from the bore to adjoin the side surfaces and the radial outward surface of the washer before passing back into the bore.

6. The flosser in accordance with claim 5, the washer being disposed for receiving the floss from the bore between one side surface and the shoulder, extending adjacent the radial outward surface, and extending between the other side surface and the handle before passing back into the bore and into the floss-receiving passageway.

7. The flosser according to claim 1, said washer being annular and said body other end being circular for receiving the washer therearound, the body other end including an up-stand boss and the washer including a notch adapted to engage the boss to prevent rotation of the washer about the body other end.

8. A dental flossing utensil having a floss-receiving cavity and a body having a pair of spaced-apart floss-carrying prongs comprising:
- an enclosed floss-receiving passageway in the body extending from the cavity to the tip of one of the prongs;
- a threaded portion on the body circumscribing the passageway proximate the cavity;
- a floss-receiving bore extending through the threaded portion into communication with the passageway and oriented generally transverse thereto;
- washer means shiftably mounted adjacent said bore and adapted for receiving floss from said bore looped therearound;
- a shoulder coupled to the floss utensil proximate to the washer means; and
- compression means mounted on the threaded portion and having an abutment for shifting said washer means with floss looped therearound towards said shoulder for compressing floss between the shoulder and washer means and between the abutment and washer means to prevent shifting movement of the floss, the compression means being configured to overlie the washer to prevent exposure of the floss from the cavity to said tip of said one prong.

9. The utensil in accordance with claim 8, wherein said washer means comprises an annular washer at least partially circling a portion of the floss utensil.

10. The utensil in accordance with claim 9, said annular washer having a notch adapted for fitting to an upstanding boss on the floss utensil to prevent rotation of the washer about the floss utensil.

11. The utensil in acordance with claim 8, said compression means including a complementally threaded nut mechanism shiftable towards said shoulder.

12. The utensil in accordance with claim 8, said compression means including an elongated handle carrying said cavity and complementally threaded for reception on said threaded portion.

* * * * *